U.S. Patent No.: US 12,422,434 B2
Date of Patent: Sep. 23, 2025

United States Patent
Gainey et al.

(54) SYSTEMS AND PROCESSES TO SCREEN FOR SEVERE ACUTE RESPIRATORY SYNDROME CORONAVIRUS 2 (SARS-CoV-2) OF 2019 (COVID-19)

(71) Applicant: BATTELLE MEMORIAL INSTITUTE, Columbus, OH (US)

(72) Inventors: Melicia R. Gainey, Columbus, OH (US); Dalia Natour, Columbus, OH (US)

( * ) Notice: Subject to any disclaimer, the term of this patent is extended or adjusted under 35 U.S.C. 154(b) by 0 days.

(21) Appl. No.: 18/441,086

(22) Filed: Feb. 14, 2024

(65) Prior Publication Data

US 2024/0192212 A1   Jun. 13, 2024

Related U.S. Application Data

(62) Division of application No. 17/337,022, filed on Jun. 2, 2021, now Pat. No. 11,921,114.

(60) Provisional application No. 63/041,551, filed on Jun. 19, 2020, provisional application No. 63/033,276, filed on Jun. 2, 2020.

(51) Int. Cl.

| | |
|---|---|
| *G01N 33/569* | (2006.01) |
| *C07K 16/10* | (2006.01) |
| *G01N 33/543* | (2006.01) |
| *C12N 5/071* | (2010.01) |

(52) U.S. Cl.
CPC ... *G01N 33/56983* (2013.01); *C07K 16/1003* (2023.08); *G01N 33/543* (2013.01); *C07K 2317/20* (2013.01); *C12N 5/0686* (2013.01); *C12N 2523/00* (2013.01); *G01N 2333/165* (2013.01)

(58) Field of Classification Search
CPC ............ C07K 16/1003; C12N 2523/00; C12N 5/0686; G01N 2333/165; G01N 2470/04; G01N 33/543; G01N 2470/00; G01N 33/56983

See application file for complete search history.

(56) References Cited

PUBLICATIONS

Notification of Transmittal with International Search Report and the Written Opinion of the International Searching Authority for International Patent Application No. PCT/US2021/035457; European Patent Office; Rijswijk, Netherlands; date of mailing Sep. 2, 2021.

Zhiqiang Zheng et al.; "Monoclonal antibodies for the S2 subunit of spike of SARS-CoV cross-react with the newly-emerged SARS-CoV-2"; bioRxiv; Mar. 7, 2020.

Szu-Chia Lai et al.; "Characterization of neutralizing monoclonal antibodies recognizing a 15-residues epitope on the spike protein HR2 region of severe acute respiratory syndrome coronavirus (SARS-CoV)"; Journal of Biomedical Science; Oct. 1, 2005.

Notification of Transmittal with International Search Report and the Written Opinion of the International Searching Authority for International Patent Application No. PCT/US2021/035335; European Patent Office; Rijswijk, Netherlands; date of mailing Sep. 2, 2021.

*Primary Examiner* — Bao Q Li

(74) *Attorney, Agent, or Firm* — Thomas E. Lees, LLC

(57) ABSTRACT

Alternative antibodies to screen for SARS-CoV-2 are disclosed. One alternative antibody is Mouse Species Coronavirus (COVID-19, MERS, and SARS-CoV NP) Antibody, Catalog Number HM1056 ("E3-Antibody" or "E3"), from EastCoast Bio, Inc., PO Box 489, North Berwick, ME 03906, USA ("EastCoast Bio"). Another alternative antibody is a combination of the E3-Antibody and Mouse Species Coronavirus (COVID-19, MERS, and SARS-CoV NP) Antibody, Catalog Number HM1057 ("E1-Antibody" or "E1"), from EastCoast Bio (the combination of the E1-Antibody and the E3-Antibody is designated as "E1/E3-Antibody" or simply "E1/E3"). Yet another alternative antibody is a combination of Mouse Species Anti-SARS-CoV-2 NP mAb, clone 4B21, Catalog Number CABT-CS027 ("C4-Antibody" or "C4"), from Creative Diagnostics, 45-1 Ramsey Road, Shirley, NY 11967, USA ("Creative Diagnostics"), and Mouse Species Anti-SARS-CoV-2 NP mAb, clone 7G21, Catalog Number CABT-CS026 ("C5-Antibody" or "C5"), also from Creative Diagnostics (the combination of the C4-Antibody and the C5-Antibody is designated as "C4/C5-Antibody" or simply "C4/C5").

11 Claims, 7 Drawing Sheets

Antibody Panel Tested:

| Description | Abbreviation | Species | Supplier | Catalog Number |
|---|---|---|---|---|
| Coronavirus (COVID-19, MERS, & SARS-CoV NP) Antibody | E3 | Mouse | East Coast Bio | HM1056 |
| Coronavirus (COVID-19, MERS, & SARS-CoV NP) Antibody | E1/E2 | Mouse | East Coast Bio | HM1057 |
| Coronavirus (COVID-19, MERS, & SARS-CoV NP) Antibody | E1/E3 | Mouse | East Coast Bio | HM1058 |
| Coronavirus (COVID-19, MERS, & SARS-CoV NP) Antibody | E1/E3 | Mouse | East Coast Bio | HM1057 |
| Coronavirus (COVID-19, MERS, & SARS-CoV NP) Antibody | E2/E3 | Mouse | East Coast Bio | HM1058 |
| Coronavirus (COVID-19, MERS, & SARS-CoV NP) Antibody | | Mouse | East Coast Bio | HM1056 |
| Mouse anti-SARS-CoV-2 NP mAb, clone 4B21 | C4/C5 | Mouse | Creative Diagnostics | CABT-CS027 |
| Mouse anti-SARS-CoV-2 NP mAb, clone 7G21 | | Mouse | Creative Diagnostics | CABT-CS026 |
| Coronavirus (COVID-19, MERS, & SARS-CoV NP) Antibody | E1/C5 | Mouse | East Coast Bio | HM1057 |
| Mouse anti-SARS-CoV-2 NP mAb, clone 7G21 | | Mouse | Creative Diagnostics | CABT-CS026 |

FIG. 1

Absorbance (490 nm with 405 nm Reference Results After 14-15 Hours of Incubation Mouse Secondary at 1:1,000

| Primary Ab Dilution | 200 TCID₅₀/well | | | | | | Mouse Conjugate 1:1,000 | | | Inoculation Media | | | |
|---|---|---|---|---|---|---|---|---|---|---|---|---|---|
| | E3 | E1/E2 | E1/E3 | E2/E3 | C4/C5 | E1/C5 | E3 | E1/E2 | E1/E3 | E2/E3 | C4/C5 | E1/C5 |
| 1:100 | 0.186 | 0.616 | 0.347 | 0.347 | 0.297 | 0.398 | 0.122 | 0.205 | 0.160 | 0.126 | 0.309 | 0.414 |
| 1:200 | 0.440 | 0.607 | 0.540 | 0.513 | 0.622 | 0.675 | 0.300 | 0.575 | 0.420 | 0.482 | 0.461 | 0.688 |
| 1:400 | 0.328 | 0.455 | 0.359 | 0.330 | 0.389 | 0.435 | 0.230 | 0.343 | 0.255 | 0.275 | 0.416 | 0.472 |
| 1:800 | 0.309 | 0.359 | 0.329 | 0.256 | 0.390 | 0.304 | 0.192 | 0.261 | 0.229 | 0.240 | 0.292 | 0.372 |
| 1:1600 | 0.291 | 0.322 | 0.278 | 0.238 | 0.284 | 0.296 | 0.204 | 0.221 | 0.091 | 0.192 | 0.046 | 0.148 |
| 1:3200 | 0.257 | 0.249 | 0.220 | 0.193 | 0.243 | 0.260 | 0.178 | 0.190 | 0.209 | 0.198 | 0.226 | 0.240 |
| 1:6400 | 0.265 | 0.253 | 0.246 | 0.222 | 0.253 | 0.258 | 0.193 | 0.194 | 0.205 | 0.204 | 0.220 | 0.249 |
| 1:12800 | 0.045 | 0.091 | 0.098 | 0.247 | 0.244 | 0.239 | 0.226 | 0.247 | 0.231 | 0.239 | 0.181 | 0.165 |

FIG. 2

Absorbance (490 nm with 405 nm Reference Results After 24 Hours of Incubation Mouse Secondary at 1:1,000

| | 200 TCID$_{50}$/well | | | | | | Inoculation Media | | | | | |
|---|---|---|---|---|---|---|---|---|---|---|---|---|
| | | | | | | | Mouse Conjugate 1:1,000 | | | | | |
| Primary Ab Dilution | E3 | E1/E2 | E1/E3 | E2/E3 | C4/C5 | E1/C5 | E3 | E1/E2 | E1/E3 | E2/E3 | C4/C5 | E1/C5 |
| 1:100 | 1.425 | 1.680 | 1.685 | 1.397 | 1.796 | 1.817 | 0.511 | 1.087 | 0.597 | 0.739 | 0.491 | 1.052 |
| 1:200 | 1.432 | 1.379 | 1.179 | 0.975 | 1.483 | 1.242 | 0.402 | 0.672 | 0.584 | 0.515 | 0.575 | 0.753 |
| 1:400 | 0.981 | 1.094 | 0.902 | 0.866 | 1.120 | 1.106 | 0.236 | 0.359 | 0.391 | 0.377 | 0.422 | 0.601 |
| 1:800 | 0.931 | 1.229 | 0.919 | 0.799 | 1.015 | 1.113 | 0.297 | 0.344 | 0.270 | 0.363 | 0.356 | 0.403 |
| 1:1600 | 1.016 | 0.956 | 0.802 | 0.577 | 0.951 | 0.921 | 0.280 | 0.300 | 0.064 | 0.334 | 0.050 | 0.338 |
| 1:3200 | 0.626 | 0.979 | 0.799 | 0.514 | 0.809 | 1.011 | 0.202 | 0.271 | 0.242 | 0.221 | 0.277 | 0.252 |
| 1:6400 | 0.463 | 0.741 | 0.870 | 0.556 | 0.847 | 0.894 | 0.174 | 0.193 | 0.204 | 0.205 | 0.207 | 0.267 |
| 1:12800 | 0.574 | 0.548 | 0.655 | 0.491 | 0.496 | 0.906 | 0.206 | 0.175 | 0.175 | 0.184 | 0.210 | 0.199 |

FIG. 3

Binding Ratios of Mouse Primary Antibody Optimization 24 Hours Post-Infection with Mouse Secondary at 1:1,000 Dilution

| Primary Ab Dilution | E3 | E1/E2 | E1/E3 | E2/E3 | C4/C5 | E1/C5 |
|---|---|---|---|---|---|---|
| 1:100 | 2.79 | 1.55 | 2.82 | 1.89 | 3.66 | 1.73 |
| 1:200 | 3.56 | 2.05 | 2.02 | 1.89 | 2.58 | 1.65 |
| 1:400 | 4.16 | 3.05 | 2.31 | 2.30 | 2.65 | 1.84 |
| 1:800 | 3.13 | 3.57 | 3.40 | 2.20 | 2.85 | 2.76 |
| 1:1600 | 3.63 | 3.19 | 12.53 | 1.73 | 19.02 | 2.72 |
| 1:3200 | 3.10 | 3.61 | 3.30 | 2.33 | 2.92 | 4.01 |
| 1:6400 | 2.66 | 3.84 | 4.26 | 2.71 | 4.09 | 3.35 |
| 1:12800 | 2.79 | 3.13 | 3.74 | 2.67 | 2.36 | 4.55 |

FIG. 4

| Serum Dilution | Mouse Anti-NP mAb HM1056 and HM1057 at 1:400; Mouse Conjugate at 1:1000 24 Hours Post-Infection; Inoculum Removed and Washed | | | | | | | | | | | |
|---|---|---|---|---|---|---|---|---|---|---|---|---|
| | 1817 | 1817 | 1827 | 1827 | 1942 | 1942 | 1899 | 1899 | 1818 | 1818 Serum only | VC | CC |
| 1:10 | 0.806 | 0.736 | 0.737 | 0.711 | 0.706 | 0.752 | 0.614 | 0.516 | 0.437 | 0.189 | 0.095 | 0.542 |
| 1:20 | 0.774 | 0.696 | 0.679 | 0.641 | 0.636 | 0.631 | 0.651 | 0.772 | 0.670 | 0.598 | 0.891 | 0.782 |
| 1:40 | 0.843 | 0.691 | 0.671 | 0.652 | 0.642 | 0.586 | 0.630 | 0.653 | 0.617 | 0.624 | 0.781 | 0.699 |
| 1:80 | 0.816 | 0.724 | 0.702 | 0.635 | 0.676 | 0.639 | 0.669 | 0.649 | 0.678 | 0.663 | 0.464 | 0.756 |
| 1:160 | 0.771 | 0.695 | 0.672 | 0.627 | 0.596 | 0.746 | 0.611 | 0.603 | 0.622 | 0.632 | 0.095 | 0.593 |
| 1:320 | 0.769 | 0.741 | 0.749 | 0.695 | 0.647 | 0.668 | 0.726 | 0.716 | 0.807 | 0.753 | 0.688 | 0.943 |
| 1:640 | 0.863 | 0.709 | 0.745 | 0.722 | 0.777 | 0.681 | 0.744 | 0.719 | 0.719 | 0.733 | 0.758 | 0.682 |
| 1:1280 | 1.228 | 0.642 | 0.560 | 0.605 | 0.663 | 0.610 | 0.639 | 0.677 | 0.715 | 0.738 | 0.515 | 0.868 |
| Endpoint | <10 | <10 | <10 | <10 | <10 | <10 | <10 | <10 | <10 | AVG: | 0.536 | 0.733 |

FIG. 5

| Serum Dilution | Mouse Anti-NP mAb HM1056 and HM1057 at 1:400; Mouse Conjugate at 1:1000 48 Hours Post-Infection; Inoculum Removed and Washed ||||||||||| |
| --- | --- | --- | --- | --- | --- | --- | --- | --- | --- | --- | --- |
| | 1817 | 1817 | 1827 | 1827 | 1942 | 1942 | 1899 | 1899 | 1818 | 1818 Serum only | VC | CC |
| 1:10 | 0.625 | 0.572 | 0.537 | 0.549 | 0.369 | 0.545 | 0.599 | 0.450 | 0.530 | 0.570 | 0.555 | 0.490 |
| 1:20 | 0.563 | 0.529 | 0.488 | 0.486 | 0.484 | 0.470 | 0.457 | 0.485 | 0.544 | 0.510 | 0.455 | 0.485 |
| 1:40 | 0.574 | 0.436 | 0.465 | 0.442 | 0.405 | 0.425 | 0.430 | 0.430 | 0.462 | 0.456 | 1.745 | 0.424 |
| 1:80 | 0.552 | 0.487 | 0.446 | 0.453 | 0.484 | 0.447 | 0.446 | 0.423 | 0.459 | 0.455 | 0.509 | 0.532 |
| 1:160 | 0.580 | 0.459 | 0.483 | 0.481 | 0.434 | 0.403 | 0.434 | 0.425 | 0.457 | 0.463 | 0.637 | 0.567 |
| 1:320 | 0.363 | 0.106 | 0.211 | 0.232 | 0.147 | 0.351 | 0.445 | 0.417 | 1.744 | 0.433 | 0.576 | 0.585 |
| 1:640 | 0.554 | 0.246 | 0.349 | 0.489 | 0.158 | 0.322 | 0.288 | 0.337 | 0.256 | 0.375 | 0.443 | 0.572 |
| 1:1280 | 1.730 | 0.518 | 0.584 | 0.582 | 0.382 | 1.961 | 0.491 | 0.487 | 0.530 | 0.499 | 1.928 | 0.542 |
| Endpoint | 640 | >1280[a] | >1280 | >1280 | >1280 | 640 | >1280 | >1280 | 160 | AVG: | 0.856 | 0.525 |
| Endpoint | 1280[a] | | >1280 | | 1280[a] | | >1280 | | 160 | | | |

| | 1817 Rep 1 | 1817 Rep 2 | 1827 Rep 1 | 1827 Rep 2 | 1942 Rep 1 | 1942 Rep 2 | 1899 Rep 1 | 1899 Rep 2 | 1818 with Virus | 1818 without Virus |
|---|---|---|---|---|---|---|---|---|---|---|
| CPE at 5 days | 320 | 320 | >1280 | >1280 | 320 | >1280 | >1280 | >1280 | All positive | All negative |
| E3/E1 primary antibody at 24 hours | UD | UD | UD | UD | UD | UD | UD | UD | UD | UD |
| E3/E1 primary antibody at 48 hours | 640 | >1280 | >1280 | >1280 | >1280 | 640 | >1280 | >1280 | 160 | All negative |

UD = Undetermined

SYSTEMS AND PROCESSES TO SCREEN FOR SEVERE ACUTE RESPIRATORY SYNDROME CORONAVIRUS 2 (SARS-CoV-2) OF 2019 (COVID-19)

CROSS REFERENCE TO RELATED APPLICATIONS

This application is a divisional application of prior application Ser. No. 17/337,022, filed 2021 Jun. 2, having the title SYSTEMS AND PROCESSES TO SCREEN FOR SEVERE ACUTE RESPIRATORY SYNDROME CORONAVIRUS 2 (SARS-CoV-2) OF 2019 (COVID-19), which claims the benefit of U.S. Provisional Patent Application Ser. No. 63/041,551, filed 2020 Jun. 19, having the title SYSTEMS AND PROCESSES TO SCREEN FOR SEVERE ACUTE RESPIRATORY SYNDROME CORONAVIRUS 2 (SARS-CoV-2) OF 2019 (COVID-19), and, also, claims the benefit of U.S. Provisional Patent Application Ser. No. 63/033,276, filed 2020 Jun. 2, having the title SYSTEMS AND PROCESSES TO SCREEN FOR SEVERE ACUTE RESPIRATORY SYNDROME CORONAVIRUS 2 (SARS-CoV-2) OF 2019 (COVID-19), the disclosures of which are all hereby incorporated by reference as if expressly set forth in their entireties.

BACKGROUND

Field of the Disclosure

The present disclosure relates generally to Severe Acute Respiratory Syndrome (SARS) Coronavirus 2 (CoV-2) and, more particularly, to systems and processes to screen for SARS-CoV-2.

Description of Related Art

Screening for a virus, such as the Severe Acute Respiratory Syndrome Coronavirus-2 (SARS-CoV-2) of 2019 (COVID-19), can be done using Enzyme Linked Immunosorbent Assay (ELISA). ELISA involves at least one antibody with specificity for a particular antigen. Consequently, during a pandemic (such as the COVID-19 pandemic) there can be a shortage of supplies needed for ELISA.

SUMMARY

The present disclosure provides systems and processes to screen for SARS-CoV-2. Briefly described, one embodiment comprises a process that uses an alternative antibody for ELISA. For some embodiments, the alternative antibody is Mouse Species Coronavirus (COVID-19, MERS, and SARS-CoV NP) Antibody, Catalog Number HM1056 ("E3-Antibody" or "E3"), from EastCoast Bio, Inc., PO Box 489, North Berwick, ME 03906, USA ("EastCoast Bio"). For other embodiments, the alternative antibody is a combination of the E3-Antibody and Mouse Species Coronavirus (COVID-19, MERS, and SARS-CoV NP) Antibody, Catalog Number HM1057 ("E1-Antibody" or "E1"), from EastCoast Bio (the combination of the E1-Antibody and the E3-Antibody is designated as "E1/E3-Antibody" or simply "E1/E3"). In yet another embodiment, the alternative antibody is a combination of Mouse Species Anti-SARS-CoV-2 NP mAb, clone 4B21, Catalog Number CABT-CS027 ("C4-Antibody" or "C4"), from Creative Diagnostics, 45-1 Ramsey Road, Shirley, NY 11967, USA ("Creative Diagnostics"), and Mouse Species Anti-SARS-CoV-2 NP mAb, clone 7G21, Catalog Number CABT-CS026 ("C5-Antibody" or "C5"), also from Creative Diagnostics (the combination of the C4-Antibody and the C5-Antibody is designated as "C4/C5-Antibody" or simply "C4/C5").

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is a chart showing different antibody panels tested.

FIG. 2 is a chart showing results after fourteen (14) hours of incubation of Severe Acute Respiratory Syndrome Coronavirus-2 (SARS-CoV-2) within a Vero E6 cell monolayer before fixation for Enzyme Linked Immunosorbent Assay (ELISA).

FIG. 3 is a chart showing results after twenty-four (24) hours of incubation of the SARS-CoV-2 within a Vero E6 cell monolayer before fixation for ELISA.

FIG. 4 is a chart showing binding ratios as a measure of signal to noise ratio (SNR) for the results of FIG. 3.

FIG. 5 is a chart showing results of measured optical densities after 24 hours of incubation for de-identified sera obtained from hospitalized patients that have tested positive for SARS-CoV-2.

FIG. 6 is a chart showing results of measured optical densities after 48 hours of incubation for de-identified sera obtained from hospitalized patients that have tested positive for SARS-CoV-2.

FIG. 7 is a chart showing results for microneutralization (MN) assay titers using a serum-removal process that used a particular primary antibody, with the results being shown for 24 hours incubation, 48 hours incubation, and a cytopathic effect (CPE) readout at approximately five (5) days.

DETAILED DESCRIPTION OF THE EMBODIMENTS

Screening for a virus, such as the Severe Acute Respiratory Syndrome Coronavirus-2 (SARS-CoV-2) of 2019 (COVID-19), can be done using Enzyme Linked Immunosorbent Assay (ELISA). ELISA involves at least one antibody with specificity for a particular antigen. When there is no global emergency, such as a pandemic, there is sufficient supply of materials to perform ELISA virus-screening processes. However, as one can imagine, during a pandemic (such as the COVID-19 pandemic) demand for the materials becomes far greater than the supply for ELISA screening processes. The antibody-antigen specificity further exacerbates the supply-and-demand problem because only a limited number of suitable materials can be used during ELISA screening. Furthermore, the problems associated with over-demand is amplified when the cause of the pandemic is a novel virus (such as in COVID-19).

To mitigate this problem, the present disclosure provides alternative antibodies for ELISA, thereby alleviating the supply-and-demand problems that can arise (and have indeed arisen during the COVID-19 pandemic). For some embodiments, one alternative antibody is Mouse Species Coronavirus (COVID-19, MERS, and SARS-CoV NP) Antibody, Catalog Number HM1056 ("E3-Antibody" or "E3"), from EastCoast Bio, Inc., PO Box 489, North Berwick, ME 03906, USA ("EastCoast Bio"). For other embodiments, another alternative antibody is a combination of the E3-Antibody and Mouse Species Coronavirus (COVID-19, MERS, and SARS-CoV NP) Antibody, Catalog Number HM1057 ("E1-Antibody" or "E1"), from EastCoast Bio (the combination of the E1-Antibody and the E3-Antibody is designated as "E1/E3-Antibody" or simply "E1/E3"). For other embodiments, yet another alternative antibody is a combination of Mouse Species Anti-SARS-CoV-2 NP mAb, clone 4B21, Catalog Number CABT-CS027 ("C4-Antibody" or "C4"), from Creative Diagnostics, 45-1 Ramsey Road, Shirley, NY 11967, USA ("Creative Diagnostics"), and Mouse Species Anti-SARS-CoV-2 NP mAb, clone 7G21, Catalog Number CABT-CS026 ("C5-Antibody" or "C5"), also from Creative Diagnostics (the combination of the C4-Antibody and the C5-Antibody is designated as "C4/C5-Antibody" or simply "C4/C5"). By providing at least three (3) additional alternative antibodies (namely, E3, E1/E3, and C4/C5), this disclosure expands considerably the supply of materials that can be used for ELISA-based COVID-19 testing.

Having provided a broad technical solution to a technical problem, reference is now made in detail to the description of the embodiments as illustrated in the drawings. Specifically, FIG. 1 shows different antibody panels tested. FIG. 2 shows results after fourteen to fifteen (14-15) hours of incubation prior to fixation of the plate and the conduct of the ELISA, while FIG. 3 shows results after twenty-four (24) hours of incubation prior to fixation of the plate and the conduct of the ELISA, for each of the panels of FIG. 1. To better display the results of FIG. 3, a chart showing binding ratios as a measure of the signal to noise ratio (SNR) for the results of FIG. 3 is shown in FIG. 4. Although several embodiments are described in connection with these drawings, there is no intent to limit the disclosure to the embodiment or embodiments disclosed herein. On the contrary, the intent is to cover all alternatives, modifications, and equivalents.

Particularly, FIG. 1 shows six (6) different antibody panels tested with the description, abbreviation, species, supplier, and catalog number shown for each antibody panel tested. The antibody panels include:

(1) Mouse Species Coronavirus (COVID-19, MERS, and SARS-CoV NP) Antibody, Catalog Number HM1056 ("E3"), from EastCoast Bio;
(2) Mouse Species Coronavirus (COVID-19, MERS, and SARS-CoV NP) Antibody, Catalog Number HM1057 ("E1"), from EastCoast Bio, in combination with Mouse Species Coronavirus (COVID-19, MERS, and SARS-CoV NP) Antibody, Catalog Number HM1058 ("E2"), also from EastCoast Bio (the combination of E1 and E2 is designated as "E1/E2");
(3) E1 in combination with E3 (designated as "E1/E3");
(4) E2 in combination with E3 (designated as "E2/E3");
(5) Mouse Species Anti-SARS-Cov-2 NP mAb, clone 4B21, Catalog Number CABT-CS027 ("C4"), from Creative Diagnostics, in combination with Mouse Species Anti-SARS-Cov-2 NP mAb, clone 4B21, Catalog Number CABT-CS026 ("C5"), also from Creative Diagnostics (the combination of C4 and C5 is designated as "C4/C5"); and
(6) E1 in combination with C5 (designated as "E1/C5").

To determine which antibodies or combinations of antibodies can be used to detect SARS-CoV-2 using in situ ELISA, a plate was coated with a monolayer of Vero E6 cells. The Vero E6-coated plates were then inoculated with 2,000 (2e3) fifty-percent-tissue-culture-infective-dose-assays-per-milliliter ($TCID_{50}$/mL, also designated as median-tissue-culture-infectious dose) SARS-CoV-2. In particular, two (2) 96-well microtiter Vero E6 plates were prepared in which each plate was fixed with a fixative of eighty percent (80%) acetone and incubated at room temperature (however, other fixatives may be used). One of the 96-well configurations was incubated for fourteen (14) to fifteen (15) hours, while the other of the 96-well configurations was incubated for twenty-four (24) hours prior to fixation with a fixative (e.g., acetone, methanol, formalin). The volume per well was approximately 150 microliters (~150 μL). The fixative was then removed, and the plates were allowed to air dry in a class II biological safety cabinets (BSC II).

Each plate was washed at least three (3) times with ~300 μL/well of wash buffer for each wash. Thereafter, the primary antibody was added. Specifically, ~297 μL of blocking buffer and ~3 μL of antibody was used for the primary antibody incubation. Multiple titrations were performed to obtain different serial two-fold down dilutions of 1:100, 1:200, 1:400, 1:800, 1:1600, 1:3200, 1:6400, and 1:12800 for a total of eight (8) concentrations for each antibody panel. The six (6) different antibody panels with six (6) corresponding controls (blanks), each having eight (8) different concentrations, resulted in a total of 96 wells (12×8=96). After the primary antibody was added, the plates were incubated at ~37±2° C. for ~60±5 min.

To the extent that there was a secondary antibody, each plate was washed at least three (3) times with ~300 μL of wash buffer for each wash. Thereafter, the secondary antibody was then added and incubated at ~37±2° C. for ~60±5 min. For the secondary antibody, the volume of blocking buffer for each plate was ~11 mL, with the volume of anti-mouse immunoglobulin G conjugate (e.g., horseradish peroxidase) being ~11 μL. The final dilution for the conjugate (secondary antibody) was approximately 1:1000.

Each plate was then washed at least three (3) times with ~300 μL of wash buffer for each wash. Thereafter, the ABTS solution (2,2'-azino-bis(3-ethylbenzothiazoline-6-sulfonic acid)) was then added and incubated at ~37±2° C. for ~30±5 min and a stop solution was immediately applied after the incubation with ABTS solution. The optical density (OD) of each plate was then read at 405 nanometers (nm) with a 490 nm reference filter. FIG. 2 shows the OD for each well in the first 96-wells microtiter Vero E6-plates configuration for the approximately 14-hour to 15-hour incubation, while FIG. 3 shows the corresponding OD in the second 96-wells microtiter Vero E6-plates configuration for the 24-hour incubation.

As shown in FIG. 2, all of the OD values at 14-15 hours were below 0.7. In other words, the OD in the infected wells (left six (6) columns (1-6)) and the OD in the uninfected wells (right six (6) columns (7-12)) for all of the titrations (1:100 through 1:12800) exhibited a low OD. Although a few infected wells exhibited an OD that was greater than the OD of its corresponding uninfected well, all of the infected OD exhibited a less-than-two-fold OD when compared to its corresponding uninfected well. Stated differently, viral infection of COVID-19 could not be readily determined at 14-hours of incubation.

Unlike FIG. 2, several of the results in FIG. 3 exhibited both: (a) a larger-than-0.7 OD; and (b) a greater-than-two-fold increase in OD in the infected wells when compared to the OD of the corresponding uninfected wells. For convenience, the binding ratios (or signal-to-noise ratio (SNR)) for FIG. 3 are shown in FIG. 4. In other words, each value in FIG. 4 represents a straightforward division of the OD of the infected well (which is designated as the signal) by the OD of the uninfected well (which is considered as noise). Thus, $SNR=OD_{infected}/OD_{uninfected}$, which is what FIG. 4 shows.

As shown in FIG. 4, high binding ratios (and consequently high SNR) was observed from the C4/C5 combination, the E1/E3 combination, and the E3-antibody. These results show that there are now alternative antibody panels that can be used to detect SARS-CoV-2 in a Vero E6 monolayer after 24-hours of infection. These alternative antibody panels provide additional options for manufacturers and, consequently, relieve some of the supply-and-demand problems associated with reagents that are needed for COVID-19 screening.

In yet other embodiments, specific steps in the in situ ELISA process are modified for use in both $TCID_{50}$ assays and microneutralization (MN) assays. Insofar as $TCID_{50}$-related processes are discussed above (in which the inoculum does not include serum), the following description focuses on processes that are applicable to MN assays (in which the inoculum includes both serum and virus).

By way of example, one embodiment of the process applicable to MN assays (designated herein as MN-assay-process for convenience) comprises coating a plate with a monolayer of Vero E6 cells and inoculating the coated plate with a predetermined amount of an inoculum. For some embodiments applicable to MN assays, the inoculum comprises both diluted serum (preferably from a patient) and a fixed amount of virus (in this case, for Severe Acute Respiratory Syndrome Coronavirus-2 (SARS-CoV-2)). The actual experimental inoculum included de-identified patient serum samples obtained from a hospital at Ohio State University (OSU), which were numerically labeled (to exclude patient-identifying information (e.g., 1817, 1818, 1827, 1899, 1942, or some other numerical designation that is de-coupled from patient information). Specifically, the de-identified patient samples were from patients who had tested positive for COVID-19 by an acceptable polymerase-chain reaction (PCR).

The inoculated plate was incubated for an initial incubating period of approximately one (~1) hour, at which point the serum-included inoculum was transferred to the VERO E6 cell plate. Thereafter, the plate was incubated further for a total incubating period of approximately forty-eight (~48) hours (meaning, the initial incubation period and the additional incubation period totaled ~48 hours). In the actual experiment, both the initial incubation and the additional incubation occurred at a temperature of ~37±2° C. and a carbon-dioxide ($CO_2$) content of ~5±2% $CO_2$.

After the total incubation period, the inoculation medium is removed and the plate is washed with Hanks Buffered Salt Solution (HBSS) at approximately one-hundred-and-fifty microliters per well (~150 μL/well). The HBSS wash is removed and the plate is fixed with a fixative (e.g., approximately eighty percent (~80%) acetone, methanol, formalin, etc.). The process continues with the steps of adding an antibody (i.e., a primary antibody) to the fixed plate. Although any of the antibodies recited above can be used, the data below shows results for E3 in combination (and substantially equal proportions) with E1 and, more particularly, to the E3/E1 combination diluted to 1:400. In some embodiments, a secondary antibody may be added and the plate is incubated at ~37±2° C. for ~60±5 min. For the secondary antibody, the volume of blocking buffer for each plate was ~11 mL, with the volume of anti-mouse immunoglobulin G conjugate (e.g., horseradish peroxidase) being ~11 μL. As above, the final dilution for the conjugate (secondary antibody) was approximately 1:1000

Similar to above, the process continues with applying ABTS solution, applying a stop solution to the washed plate, and thereafter reading the optical density of the plate. If the optical density is greater than a predefined threshold (here, approximately 0.7), then the process provides an indication that the sample is positive for anti-SARS-CoV-2 antibodies.

Some examples of experimental results are shown in FIGS. 5, 6, and 7, in which a 96-well plate setup was configured as follows: (a) wells designated 1A through 1H (1A-1H) and 2A-2H in FIGS. 5 and 6 contained diluted serum from a patient designated as OSU-1817 (to exclude any personal identifying information); (b) wells 3A-3H and 4A-4H contained diluted serum from patient OSU-1827; (c) wells 5A-5H and 6A-6H contained diluted serum from patient OSU-1942; (d) wells 7A-7H and 8A-8H contained diluted serum from patient OSU-1899; (e) wells 9A-9H contained diluted serum from patient OSU-1818; (f) wells 10A-10H contained the same inoculation medium as 9A-9H but without virus (designated as NV (no virus)); (g) wells 11A-11D and 12A-12D contained virus control (VC), which included the virus but without the serum; and (h) wells 11E-11H and 12E-12H contained the cell culture (CC), which included only the inoculation media (no virus and no serum).

Using this plate setup, the MN-assay-process (described above), and the E1/E3 antibody panel (also described above), data was gathered at both: (a) twenty-four (24) hours (results shown in FIG. 5); and (b) forty-eight (48) hours (results shown in FIG. 6). Both the 24-hour and 48-hour results were compared to a cytopathic effect (CPE) readout at approximately five (5) days (comparison shown in FIG. 7).

As shown in FIG. 7, the results at 24-hours was inconclusive and the results were designated as undetermined (UD). Comparatively, the results at 48-hours (when the inoculum was removed after the initial incubation period of ~1 hour) corresponded to the CPE readout, thereby confirming the presence of SARS-CoV-2 for the in situ ELISA readout of the MN assay. Given these results, it appears that removal of the inoculum after the initial hour of incubation and washing the plate prior to fixation at the end of the assay removed non-specific binding of the primary antibody (here, E1/E3), as evidenced by the numerical values in 10A-10H being similar to the CC control wells (11E-11H and 12E-12H). Thus, neutralization is observable in clinical samples from human patients at 48 hours of incubation, as shown in FIGS. 5, 6, and 7.

Any process descriptions or blocks in flow charts should be understood as being executable out of order from that shown or discussed, including substantially concurrently or in reverse order, depending on the functionality involved, as would be understood by those reasonably skilled in the art of the present disclosure.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

What is claimed is:

1. A process for performing microneutralization assays to quantify neutralizing antibodies to viruses, the process comprising:
coating a plate with a monolayer of Vero E6 cells;
inoculating the coated plate with a serum-included inoculum, the serum-included inoculum comprising:

serum from a patient, the serum being diluted; and a virus, the virus being Severe Acute Respiratory Syndrome Coronavirus-2 (SARS-COV-2);

incubating the inoculated plate;

fixing the Vero E6 cells plate;

diluting a primary antibody, the primary antibody being selected from the group consisting of:

Mouse Species Coronavirus (COVID-19, MERS, and SARS-COV NP) Antibody, Catalog Number HM1056 ("E3");

E3 in combination with Mouse Species Coronavirus (COVID-19, MERS, and SARS-CoV NP) Antibody, Catalog Number HM1057 ("E1"); and Mouse Species Anti-SARS-Cov-2 NP mAb, clone 4B21, Catalog Number CABT-CS027 ("C4") in combination with Mouse Species Anti-SARS-Cov-2 NP mAb, clone 4B21, Catalog Number CABT-CS026 ("C5");

adding the diluted primary antibody to the fixed plate;

incubating the plate having the diluted primary antibody;

washing the plate having the diluted primary antibody;

adding a secondary antibody to the plate;

incubating the plate having the secondary antibody;

washing the plate having the secondary antibody;

applying 2,2'-azino-bis(3-ethylbenzothiazoline-6-sulfonic acid) (ABTS) solution to the plate;

applying a stop solution to the plate;

reading the optical density of the plate; and determining whether the optical density is greater than approximately 0.7.

2. The process of claim 1, wherein incubating the inoculated plate comprises incubating for twenty-four (24) hours.

3. The process of claim 1, wherein incubating the inoculated plate comprises incubating for greater than 16 (sixteen) hours.

4. The process of claim 1, wherein diluting the primary antibody comprises diluting the antibody to a 1:400 concentration from its initial concentration.

5. The process of claim 1, wherein diluting the primary antibody comprises diluting the antibody to a 1:800 concentration from its initial concentration.

6. The process of claim 1, wherein diluting the primary antibody comprises diluting the antibody to a 1:1600 concentration from its initial concentration.

7. The process of claim 1, wherein diluting the primary antibody comprises diluting the antibody to a 1:3200 concentration from its initial concentration.

8. The process of claim 1, wherein diluting the primary antibody comprises diluting the antibody to a 1:6400 concentration from its initial concentration.

9. The process of claim 1, wherein diluting the primary antibody comprises diluting the antibody to a 1:12800 concentration from its initial concentration.

10. The process of claim 1, further comprising diluting the secondary antibody to a 1:1000 concentration from its initial concentration prior to adding the secondary antibody to the fixed plate.

11. The process of claim 1, further comprising washing the inoculated plate before fixing the Vero E6 cells.

* * * * *